United States Patent [19]
Harris et al.

[11] Patent Number: 5,216,185
[45] Date of Patent: Jun. 1, 1993

[54] POLYMERIZABLE CALIXARENE AND OXACALIXARENE DERIVATIVES, POLYMERS THEREOF AND USE OF SUCH DERIVATIVES AND POLYMERS FOR SEQUESTRATION OF METALS

[75] Inventors: Stephen J. Harris, Dublin; John Guthrie, County Kildare; Maureen MacManus, Dublin, all of Ireland; Michael A. McKervey, Belfast, Northern Ireland

[73] Assignee: Loctite Limited, Dublin, Ireland

[21] Appl. No.: 625,575

[22] Filed: Dec. 10, 1990

[30] Foreign Application Priority Data

Dec. 13, 1989 [IE] Ireland ................................ 3986/89

[51] Int. Cl.$^5$ ................ C07F 19/00; C07C 69/76; C07C 49/105
[52] U.S. Cl. .......................... 556/1; 560/75; 568/325; 568/631; 568/632; 568/633
[58] Field of Search .............. 556/419, 1; 560/75; 568/325, 631, 632, 633

[56] References Cited

U.S. PATENT DOCUMENTS

| | | | |
|---|---|---|---|
| 4,642,362 | 2/1987 | Harris et al. ................ | 556/419 |
| 4,882,449 | 11/1989 | Harris ................ | 556/419 |
| 4,957,960 | 9/1990 | Harris et al. ................ | 524/243 |

OTHER PUBLICATIONS

Ungaro et al., "New Ionizable Ligands from p.t-butyl-calix[4]arene," Journal of Inclusion Phenomena 2, 199-206, 1984.

Primary Examiner—Arthur C. Prescott
Attorney, Agent, or Firm—Edward K. Welch, II; Eugene F. Miller

[57] ABSTRACT

Polymerizable calixarene and oxacalixarene derivates wherein at least one aryl group of the macrocyclic ring has a phenolic side chain of the formula VII:

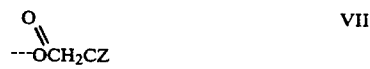

VII wherein Z is a group containing an acrylate or methacrylate functional group. Linear polymers may be formed from these compounds by free radical polymerization at the (meth)acrylate group. Such compounds and their polymers are capable of sequestering metals.

13 Claims, No Drawings

POLYMERIZABLE CALIXARENE AND OXACALIXARENE DERIVATIVES, POLYMERS THEREOF AND USE OF SUCH DERIVATIVES AND POLYMERS FOR SEQUESTRATION OF METALS

CROSS REFERENCE TO RELATED APPLICATION

This application is related to application Ser. No. 625,573 entitled "Calixarene and Oxacalixarene Derivatives and use thereof for Sequestration of Metals" filed on even date herewith.

BACKGROUND OF THE INVENTION a) Field of the Invention

This invention relates to novel calixarene and oxacalixarene derivatives, to polymers of such derivatives, and to use of the derivatives and the polymers thereof for sequestration of metals.

b) Description of the Related Art

U.S. Pat. No. 4,882,449 Harris et. al. describes nitrogen-containing calixarene derivatives selected from the groups

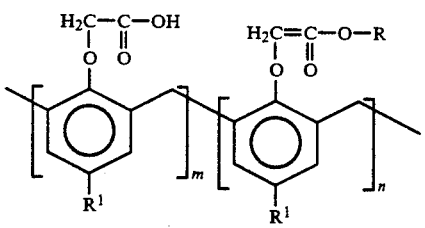

I

II

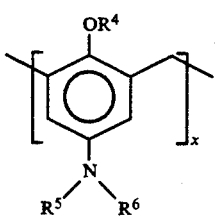

wherein
$m+n=4$, 6 or 8
$n=$ an integer 1–8
$m=$ an integer 0–7
$x=4$, 6 or 8
$R^1$ is H, alkyl, aralkyl, alkoxy, aroyl, or alkoyl,
R is aliphatic or aromatic, unsubstituted or substituted, hydrocarbyl containing nitrogen,
$R^4$ is unsubstituted or substituted hydrocarbyl, carbonyl or aryl;
$R^5$ and $R^6$ (which may be the same or different) are hydrogen, or unsubstituted or substituted hydrocarbyl.

That application also describes use of such calixarene derivatives for selectively sequestering transition metals from aqueous mixtures of alkali metals and transition metals.

European Patent Publication No. 0,309,291 (Application No. 88 308 897.3) describes oxacalixarene and calixarene derivatives of the formula III:

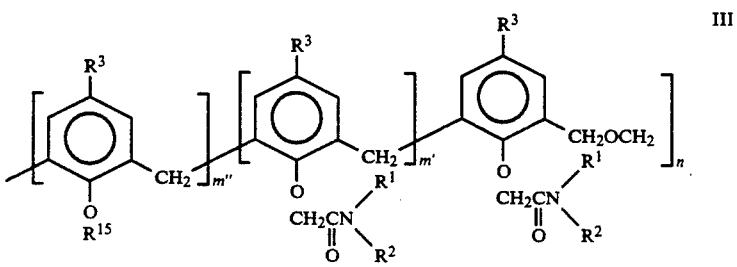

wherein
$m'+m''=0-8$
$n=0-8$
$m' \geq \frac{1}{2}(m'+m'')$
$3 \leq m'+m''+n \leq 8$
if $n=0$, $m'+m'' \geq 4$
$R^3$ is H, halogen, or hydrocarbyl, aryl, hydrocarbylaryl or a substituted derivative thereof and $R^3$ may be the same or different on each aryl group;
$R^1$ and $R^{15}$ which may be the same or different are H or hydrocarbyl, aryl, hydrocarbylaryl or a substituted derivative thereof;
$R^2$ is selected from:
$R^4$ which is H, or hydrocarbyl, aryl, hydrocarbylaryl or a substituted derivative thereof,

wherein $R^5$ and $R^6$ which may be the same or different are H, hydrocarbyl, aryl, hydrocarbylaryl, or a substituted derivative thereof,
—$OR^1$, wherein $R^1$ is as defined above,
and $R^{17}$ which is a residue of hydrocarbyl, aryl or hydrocarbylaryl group or of a substituted derivative thereof providing a bond to another oxacalixarene or calixarene derivative of formula III wherein $R^2$ is $R^{17}$.

That application also describes use of such compounds for sequestering transition metals such as copper and silver, transition series elements such as manganese, alkaline earth elements such as calcium and magnesium, and Group III elements such as aluminum in addition to alkali metals.

Our co-pending Irish Patent Application No. 3982/89 entitled "Calixarene and Oxacalixarene Derivatives and Use thereof for Sequestration of Metals" describes calixarene and oxacalixarene derivatives of the formula IV:

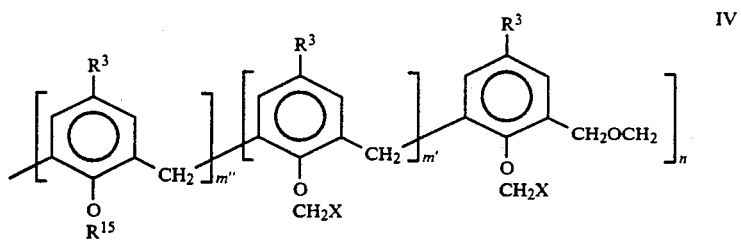

wherein
m'+m"=0-8
n=0-8
m'≧½(m'+m")
3≦m'+m"+n≦8
if n=0, m'+m"≧4

R³ is H, halogen, or hydrocarbyl, aryl, hydrocarbylaryl or a substituted derivative thereof and R³ may be the same or different on each aryl group;

R¹⁵ is H or hydrocarbyl, aryl, hydrocarbylaryl or a substituted derivative thereof;

X is selected from

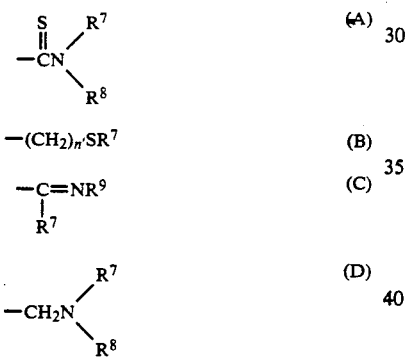

wherein
R⁷ and R⁸ which may be the same or different are H or hydrocarbyl, aryl, hydrocarbylaryl or a substituted derivative thereof;

R⁹ is —OH, —NH₂, —NHC(O)NH₂ or —NHAr, wherein Ar is aryl or a substituted derivative thereof, n' is 0 or 1.

That application also describes use of such compounds for sequestration of metals.

U.S. Pat. No. 4,699,966 Harris et al describes a polymerisable calixarene compound of the formula

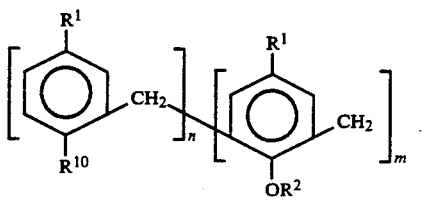

where
the R¹ groups are the same or different H or hydrocarbyl groups, the R² groups are H, hydrocarbyl, —CH₂C(=O)OR³ or —CH₂C(=O)R³;

R³ is hydrocarbyl or substituted hydrocarbyl;

R¹⁰ is an acrylate or methacrylate functional group, n is an integer of 1-8, m is an integer of 0-7 and n+m is 4-8. Such compounds may be polymerised free radically. In particular, U.S. Pat. No. 4,699,966 (and also U.S. Pat. No. 4,642,362 Harris et al) describes the preparation of an acrylated calix(6) arene of the formula

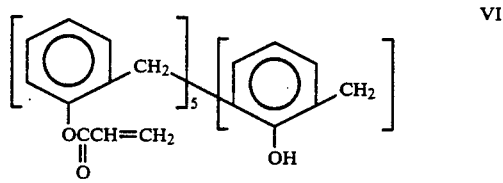

and the copolymerization thereof to a copolymer insoluble in common organic solvents. The polymer bound calixarenes of U.S. Pat. No. 4,699,966 are described generally as metal ion sequestrants. However the polymerisable calixarene compounds having acrylate or methacrylate functional groups attached directly to the aryl groups through the phenolic oxygen atoms as described in U.S. Pat. No. 4,699,966 are not particularly efficient at sequestering metals and polymers formed therefrom have little utility as metal sequestrants.

SUMMARY OF THE INVENTION

The present invention provides calixarene and oxacalixarene derivatives wherein at least one aryl group of the macrocyclic ring has a phenolic side chain of the formula VII:

wherein Z is a group containing an acrylate or methacrylate functional group.

Preferably Z is a group of the formula:

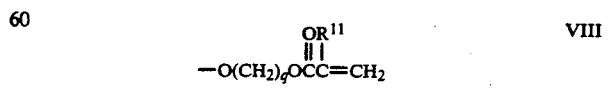

wherein
q=an integer 2-10, and,
R¹¹ is H or CH₃.

More particularly the invention provides calixarene and oxacalixarene derivatives of the formula:

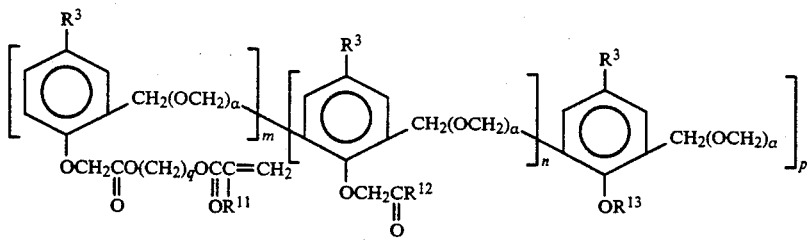

IV wherein
$3 \leq m+n+p \leq 8$
$m \geq 1$
q=an integer 2-10
a which may be the same or different on each aryl group is 0 or 1;
$R^3$ is H, halogen, hydrocarbyl, aryl, hydrocarbylaryl or a substituted derivative thereof and $R^3$ may be the same or different on each aryl group;
$R^{11}$ is as defined above;
$R^{12}$ is hydrocarbyl, aryl, hydrocarbylaryl or a substituted derivative thereof,
or $N^{12'}{}_2$ (wherein $R^{12'}$ is H, hydrocarbyl, aryl, hydrocarbylaryl or a substituted derivative thereof),
or $OR^{14}$ (wherein $R^{14}$ is hydrocarbyl, aryl, hydrocarbylaryl or a substituted derivative thereof including a N-substituted derivative thereof),
or $NHNH_2$, or NHOH or NHAr (wherein Ar is aryl or a substituted derivative thereof).
$R^{13}$ is hydrocarbyl, aryl, hydrocarbylaryl or a substituted derivative thereof,
or —$CH_2X$ wherein X is selected from

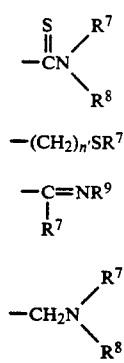

wherein
$R^7$ and $R^8$ which may be the same or different are H or hydrocarbyl (including a cycloaliphatic ring formed by $R^7$ and $R^8$ together), aryl, hydrocarbylaryl or a substituted derivative thereof;
$R^9$ is —OH, —$NH_2$, —NHC(O)$NH_2$ or —NHAr, wherein Ar is aryl or a substituted derivative thereof, and
n' is 0 or 1.
Due to the (meth)acrylate functionality, the calixarene and oxacalixarene derivatives of the present invention are capable of free radical polymerisation.

The present invention therefore also provides a polymerisable composition comprising a calixarene or oxacalixarene derivative having a phenolic side chain of the formula VII as defined above, together with a free radical polymerisation initiator.

The invention also provides polymers of calixarene and oxacalixarene derivatives having a phenolic side chain of the formula VII as defined above.

In one aspect, the present invention provides a method of sequestering metals which comprises contacting a metal-containing medium with a calixarene or oxacalixarene derivative as defined above or a polymer thereof.

The calixarene and oxacalixarene derivatives of the present invention and the polymers thereof are capable of sequestering metals such as alkali metals, transition metals, precious metals, heavy metals, lanthanides or actinides, depending upon the substituents present at $R^{12}$ and/or $R^{13}$ which have the metal sequestering ability associated with the respective substituent groups as described in our previous European Applications and co-pending Irish Application mentioned above. Due to the presence of the group —$OCH_2C(O)$— in the side chain of formula VII, the compounds of the present invention have significantly better metal sequestering ability than those described in U.S. Pat. No. 4,699,966. In polymerised form they are useful for example as ion selective resins or electrode materials which are non-leachable.

The compounds of the present invention wherein m is 1 are monofunctional and are capable of forming linear polymers which are soluble in organic solvents. This facilitates processing and renders them useful in coatings and the like which are applied from solution. The methacrylate functional calixarenes of U.S. Pat. No. 4,699,966 polymerise to cross-linked solvent-insoluble polymers only.

The compounds of the present invention may be copolymerised with other monomers to give polymers having a combination of properties. For example, monofunctional calixarene monomers may be copolymerised with multifunctional calixarene monomers or non-calixarene monomers.

The term "hydrocarbyl" as used herein means aliphatic hydrocarbyl including alkyl, alkenyl and alkynyl. Hydrocarbyl groups shall preferably contain from 1 to 10 carbon atoms, more preferably from 1 to 5 carbon atoms, and aryl and hydrocarbylaryl groups shall preferably have from 6 to 20 carbon atoms, more preferably from 6 to 10 carbon atoms. Hydrocarbyl groups are preferred, especially alkyl or alkenyl groups. A substituted derivative of the foregoing may suitably be substituted with one or more halo groups or substituted or interrupted by one or more oxo groups. Halogen may be chlorine, bromine, fluorine or iodine.

The preferred calixarene or oxacalixarene derivatives of formula IX are those in which p=0 and m+n=4 or 6. Preferably q is 2-5. Preferably $R^{12}$ is —$O(CH_2)_b CH_3$ wherein b is 1-4. Preferably $R^{11}$ is —$CH_3$.

The preparation of calixarene derivatives is known and is described, for example, in C. Gutsche et. al., Acc.

Chem. Res., 16, 161-170 (1983); in U.S. Pat. No. 4,556,700 Harris et. al., and in J. Inclusion Phenomena 2 199-206 (1984) D. Reidel Publishing Company; the appropriate disclosures of all of which are incorporated herein by reference.

The preparation of aryl calixarene derivatives is described in European Patent Publication No. 0,259,016 (Application No. 87 306 963.7) and equivalent applications in other countries.

Mixed functionality calixarene derivatives are described in European Patent Application No. 0,196,895 A2 and U.S. Pat. No. 4,642,362 Harris et. al. Aryl groups having different side chains and/or having either methylene or ether bridges may be interspersed around the ring.

Oxacalixarene compounds may be readily synthesised by methods described in C. Gutsche et. al., J. Am. Chem. Soc. 103, 3782 (1981); B. Dhawan et. al., J. Org. Chem., 48, 1536 (1983), U.S. Pat. No. 4,098,717 Buriks et. al., and European Patent Publication No. 0,309,291 (Application No. 88 308 897.3) the appropriate disclosures of which are incorporated herein by reference.

DESCRIPTION OF THE PREFERRED EMBODIMENTS

Embodiments of the invention are described below by way of Example.

EXAMPLE 1 a. Preparation

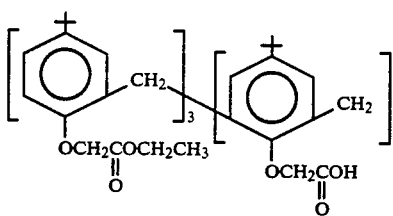

X

To 5.01 g (0.005 mole) of the tetraethylacetate of p-t-butylcalix-4-arene prepared by the method described in U.S. Pat. No. 4,556,700 Harris et al in 100 mls chloroform was added 20 drops (0.2 ml)(0.0026 mole) trifluoroacetic acid and the solution was stirred at room temperature for 22 hours. After this time the chloroform solution was washed well with water, then the organic phase was dried over dried magnesium sulphate. The volatiles were removed to give 4.9 g (100% yield) of colourless crude product. Recrystallisation from aqueous ethanol gave 4.3 g (88%) colourless crystalline title compound of formula X; m.p. 166°-9° C.

i.r. spectroscopy results $\nu$3510 (W) 3360 (W) OH, 1750(S) C=O.

Elemental analysis results: (calculated for $C_{58} H_{76} O_{12}$: C: 72.22, H 7.88; Found C 72.29, H 7.71)

b. Preparation

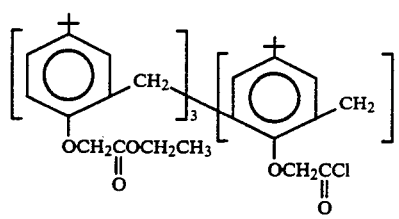

XI

To 4.15 g (0.0044 mole) of the monoacid of Example 1a was added 10 mls thionyl chloride under nitrogen with stirring. The reaction mixture was then refluxed for 2 hours, following which excess thionyl chloride was distilled off under nitrogen and the last traces at reduced pressure to give 4.3 g acid chloride title compound of formula XI as an off white solid which was not further purified in view of its moisture sensitivity.

c. Preparation

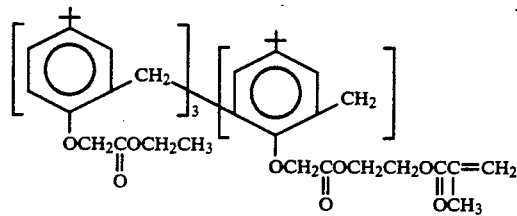

XII

To 4.3 g (0.0044 mole) of the acid chloride of Example 1b in 20 mls NaH dried THF was added dropwise with stirring under nitrogen 1.71 g (0.013 mole) 2-hydroxyethyl methacrylate, 5 mg naphthoquinone free radical stabiliser and 1.5 g (0.015 mole) triethylamine. The reaction mixture was cooled with a cool air drying gun during addition as the reaction was exothermic and a white precipitate formed. The reaction mixture was then allowed to stir at room temperature for a further 17 hours following which all volatiles were removed, the last traces at reduced pressure, and the reaction mixture was then added to the water to give an off-white solid precipitate which was filtered off, then taken up in 100 mls dichloromethane which was washed well with water and dried with dried magnesium sulphate to give after removal of volatiles 4.5 g of off-white product. Chromatography on neutral alumina using dichloromethane as eluent gave high priority title product of formula XII as a colourless solid; m.p. 63°-5°.

i.r. spectroscopy results: $\nu$1760(S) C=O(CH$_2$), 1722(S) C=O (C—CH$_3$), 1630(W) C=C.

Elemental analysis results: (Calculated for $C_{64} H_{84} O_{14}$, C: 71.35, H: 7.86, O: 20.79; Found C: 71.00, H: 7.55, O: 20.82).

EXAMPLE 2

Preparation Linear Polymer

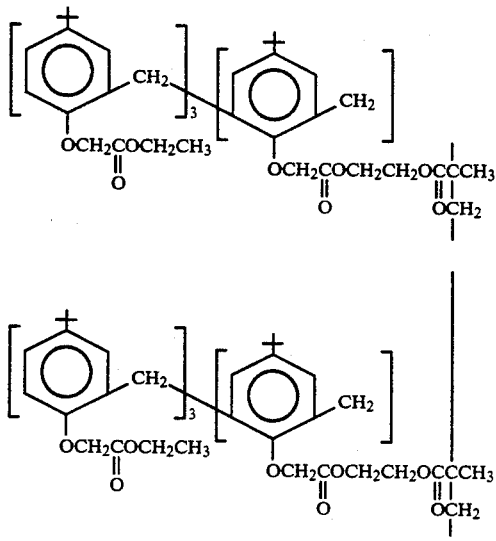

0.7 g of the compound XII from Example 1c was dissolved in 2 g toluene containing 20 mg AZBN (azoisobutyronitrile) and the resulting solution was stirred in a round bottom flask with reflux condenser on it for 17 hours immersed in an oil bath at 87° C. After this period of time the cooled reaction mixture was poured into a large volume of methanol to give a fine white solid which was washed well with more methanol to give 0.37 g linear polymer which was soluble in common organic solvents such as dichloromethane, acetone and THF.

i.r. spectroscopy results: $\nu$no C=C at 1630 cm$^{-1}$;

HPLC analysis: Waters Millipore Sugar Analyser/-liquid chromatograph; Ultrastyragel THF linear mix bed column; THF as eluent, 1.0 mls/min. R1 Detector retention volume 9.8 minutes; m.w. 6745 (mp).

EXAMPLE 3

Preparation

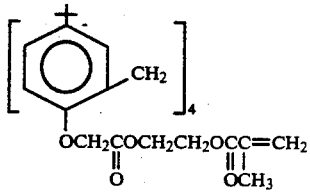

XIV

To 10.4 g (0.011 mole) acid chloride starting material

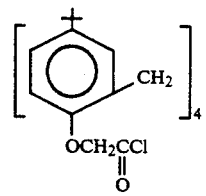

B prepared as described in European Patent Publication No. 0,259,016 (Application No. 87 306 963.7) in 100 mls NaH dried THF under nitrogen with stirring was added 11.8 g (0.091 mole) 2-hydroxyethyl methacrylate, 10 mg napththoquinone, and 9.3 g (0.091 mole) triethylamine dropwise with stirring while cooling with a cool air gun. A white precipitate formed. The reaction mixture was then stirred for a further 17 hours at room temperature after which volatiles were removed, the last traces at reduced pressure. The solid was then added to ice water and the off-white precipitate product taken up in 250 mls dichloromethane which was washed well with water, then dried with dried magnesium sulphate to give after removal of volatiles 12.9 g pale yellow oil product which solidified on standing. Chromatography on neutral alumina using dichloromethane gave high purity colourless solid title product of formula XIV; m.p. 42°–5° C.

i.r. spectroscopy results: $\nu$1760(S) C=O(CH$_2$), 1720(S) C=O (C—CH$_3$) 1633(m) C=C Elemental analysis results: (Calculated for C$_{76}$ H$_{96}$ O$_{20}$. C=68,65, H=7.28, O=24.07; Found C: 68.25, H: 7.36, O=24.10).

EXAMPLE 4

Preparation of Polymer (Crosslinked)

1 g of the compound of Example 3c was dissolved in 2 g dichloromethane to which was added 20 mg of 2,2-dimethoxy-2-phenyl acetophenone. The solvent was allowed to evaporate and the 2 mm thick resulting film was irradiated under a medium-pressure mercury arc for 180 seconds to give a clear crosslinked brittle film insoluble in all common organic solvents including acetone.

i.r. spectroscopy results: $\nu$no C=C at 1630 cm$^{-1}$.

EXAMPLE 5

Ion Extraction by Calixarenes-Neutral Sodium Picrate

The ion binding abilities of the calixarenes were measured by extraction of metal picrate from aqueous into organic media. In each experiment a solution of calixarene in dichloromethane was prepared of 2.5×10$^{-4}$M which was shaken with 2.5×10$^{-4}$M aqueous neutral sodium picrate in equal volumes of 5 ml for 3 minutes and the percentage extraction of sodium picrate into organic phase was determined by measuring the increase in absorbance of the dichloromethane layer at 378 nm in a U.V. spectrophotomer.

| Extraction Neutral Na Picrate from aqueous to CH$_2$Cl$_2$; 2.5 × 10$^{-4}$M Solutions shaken for 3 minutes. | |
|---|---|
| Compound: | Percentage Extraction |
| 1. Tetraethylacetate of p-t-butyl Calix-(4)-arene (U.S. Pat. No. 4,556,700) | 26.7 |

| Extraction Neutral Na Picrate from aqueous to CH$_2$Cl$_2$; 2.5 × 10$^{-4}$M Solutions shaken for 3 minutes. | |
| --- | --- |
| Compound: | Percentage Extraction |
| 2. Example 1c - Compound XII | 20.1 |
| 3. Example 2 Polymer - Compound XIII | 18.9 |
| 4. Example 3 - Compound XIV | 20.4 |

EXAMPLE 6

Ion Extraction by Calixarenes —Basic Sodium Picrate

In order to compare the calixarene derivatives of Example 1c and 3c herein with the methacrylate functional calixarene of formula VI described in U.S. Pat. No. 4,699,966, an extraction test was carried out with basic sodium picrate in the manner described in Example 12 of U.S. Pat. No. 4,699,966.

| Extraction Basic Na Picrate from Aqueous to CH$_2$Cl$_2$ 2.5 × 10$^{-4}$M Solutions shaken for 3 minutes | |
| --- | --- |
| Compound: | Percentage Extraction |
| Compound VI | 0 |
| Example 1c - Compound XII | 52.3 |
| Example 3 - Compound XIV | 70.0 |

We claim:

1. Calixarene and oxacalixarene derivatives wherein at least one aryl group of the macrocyclic ring has a phenolic side chain of the formula VII:

wherein Z is a group containing an acrylate or methacrylate functional group.

2. Compounds according to claim 1 wherein Z is a group of the formula:

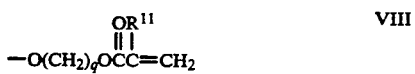

wherein
q = an integer 2-10,
R$^{11}$ is H or CH$_3$.

3. Compounds according to claim 2 wherein q is 2-5.

4. Compounds according to claim 2 wherein R$^{11}$ is —CH$_3$.

5. A compound according to claim 1 wherein the compound is of the structure:

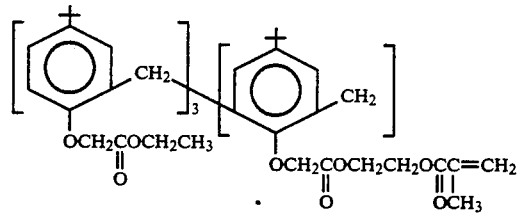

6. A compound according to claim 1 wherein the compound is of the structure:

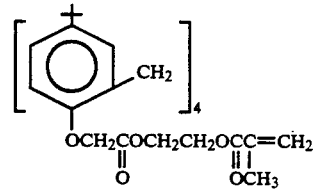

7. Calixarene and oxacalixarene derivatives of the formula:

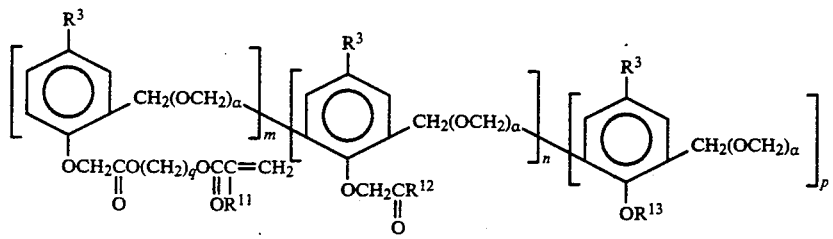

wherein
3 ≦ m+n+p ≦ 8;
m ≧ 1;
q = an integer 2-10; and
a, which may be the same or different on each aryl group, is 0 or 1;
R$^3$ is H, halogen or a hydrocarbyl, aryl or hydrocarbylaryl group or a substituted derivative thereof and R$^3$ may be the same or different on each aryl group;
R$^{11}$ is H or CH$_3$;
R$^{12}$ is hydrocarbyl, aryl, hydrocarbylaryl or a substituted derivative thereof; N(R$^{12'}$)$_2$, wherein R$^{12'}$ is H or hydrocarbyl, aryl, hydrocarbylaryl or a substituted derivative thereof; OR$^{14}$, wherein
R$^{14}$ is hydrocarbyl, aryl, hydrocarbylaryl or a substituted derivative thereof, including an N-substituted derivative thereof; —NHNH$_2$; —NHOH; or —NHAr, wherein Ar is aryl or a substituted derivative thereof;
R$^{13}$ is hydrocarbyl, aryl, hydrocarbylaryl or a substituted derivative thereof; or —CH$_2$X, wherein X is selected from

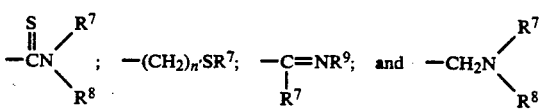

wherein $R^7$ and $R^8$, which may be the same or different, are H or hydrocarbyl (including a cycloaliphatic ring formed by $R^7$ and $R^8$ together), aryl, hydrocarbylaryl or a substituted derivative thereof;

$R^9$ is —OH, —$NH_2$, —NHC(O)$NH_2$ or —NHAr, wherein Ar is aryl or a substituted derivative thereof; and n′ is 0 or 1; and wherein a substituted derivative of a hydrocarbyl, aryl or hydrocarbylaryl group, unless otherwise specifically indicated above, refers to such groups which are substituted with one or more halo groups or substituted or interrupted by one or more oxo groups.

8. Compounds according to claim 7 wherein q is 2–5.

9. Compounds according to claim 7 wherein $R^{11}$ is —$CH_3$.

10. Compounds according to claim 7 wherein p=0.

11. Compounds according to claim 7 wherein m+n=4 and p=0.

12. Compounds according to claim 7 wherein $R^{12}$ is —O($CH_2$)$_b CH_3$ wherein b is 1–4.

13. A method of sequestering metals which comprises contacting a metal-containing medium with a compound according to claim 1 or a polymer thereof.

* * * * *